United States Patent
Favero et al.

(10) Patent No.: US 10,669,231 B2
(45) Date of Patent: Jun. 2, 2020

(54) METHOD FOR PRODUCING 2-ACRYLAMIDO-2-METHYLPROPANE SULPHONIC ACID

(71) Applicant: S.P.C.M. SA, Andrezieux Boutheon (FR)

(72) Inventors: Cédrick Favero, Andrezieux Boutheon (FR); Johann Kieffer, Andrezieux Boutheon (FR)

(73) Assignee: S.P.C.M. SA, Andrezieux Boutheon (FR)

( * ) Notice: Subject to any disclaimer, the term of this patent is extended or adjusted under 35 U.S.C. 154(b) by 0 days.

(21) Appl. No.: 16/495,207

(22) PCT Filed: Mar. 19, 2018

(86) PCT No.: PCT/FR2018/050653
§ 371 (c)(1),
(2) Date: Sep. 18, 2019

(87) PCT Pub. No.: WO2018/172677
PCT Pub. Date: Sep. 27, 2018

(65) Prior Publication Data
US 2020/0024228 A1 Jan. 23, 2020

(30) Foreign Application Priority Data
Mar. 20, 2017 (FR) .................................... 17 52289

(51) Int. Cl.
*C07C 303/20* (2006.01)
*C07C 309/15* (2006.01)
*C07C 303/44* (2006.01)

(52) U.S. Cl.
CPC .......... *C07C 303/20* (2013.01); *C07C 303/44* (2013.01); *C07C 309/15* (2013.01)

(58) Field of Classification Search
CPC ... C07C 303/02; C07C 303/20; C07C 303/44; C07C 309/15
See application file for complete search history.

(56) References Cited

U.S. PATENT DOCUMENTS

| 4,337,215 A | 6/1982 | Doi et al. |
| 6,448,347 B1 | 9/2002 | Quinn et al. |
| 8,247,601 B2 * | 8/2012 | Wakayama ........... C07C 303/02 562/105 |
| 2010/0274048 A1 * | 10/2010 | Wakayama ........... C07C 303/02 562/105 |
| 2018/0244609 A1 * | 8/2018 | Favero .................... C08F 20/58 |

FOREIGN PATENT DOCUMENTS

| CN | 102351744 A | | 2/2012 | |
| CN | 103664709 | * | 3/2014 | ........... C07C 303/44 |
| CN | 103664709 A | | 3/2014 | |
| JP | H05125037 | * | 5/1993 | ........... C07C 303/44 |
| WO | 2009/072480 A1 | | 6/2009 | |

OTHER PUBLICATIONS

JPH05125037 (JP3412158 B2); Mitsubishi Chem Ind., Production of high-purity 2-acrylamido-2-methylpropane sulfonic acid, English translation, 7 pages (Year: 1993).*
International Search Report (and English translation) and Written Opinion of the International Searching Authority for International Application No. PCT/FR2018/050653 dated Jun. 1, 2018.
Dragan, D., "On the Ritter Synthesis of N-tert-Butylacrylamide (Part II)* Reaction between tert-Butylalcohol and Acrylonitrile in Non-aqueous Solvents", Iranian J of Polymer Science and Technology, vol. 4, No. 1, pp. 42-49 (1995).
International Preliminary Report on Patentability for International Application No. PCT/FR2018/050653 dated Jun. 6, 2019.

* cited by examiner

*Primary Examiner* — Yate' K Cutliff
(74) *Attorney, Agent, or Firm* — Heslin Rotheberg Farley & Mesiti P.C.

(57) ABSTRACT

The present invention relates to a production process for 2-acrylamido-2-methylpropane sulfonic acid including at least the following successive steps:
1) mixing of acrylonitrile with at least one compound contributing $SO_3$ at a temperature included between −80 and 30° C.;
2) placing in contact and mixing isobutylene and the sulfonating mixture with a molar ratio of $SO_3$ to isobutylene included between 0.2:1 and 2:1 and a molar ratio of acrylonitrile to isobutylene included between 3:1 and 60:1 at a temperature included between −40 and 100° C.;
3) solid/liquid separation of the reaction mixture and isolation of the solid particles in the form of a composition 1;
4) mixing composition 1 at the end of step 3) with an aqueous solution A included at a temperature comprised between −20 and 70° C. in order to obtain a suspension 1 of 2-acrylamido-2-methylpropane sulfonic acid crystals;
5) solid/liquid separation of the suspension 1 and isolation of the crystals in form of composition 2.

20 Claims, No Drawings

METHOD FOR PRODUCING 2-ACRYLAMIDO-2-METHYLPROPANE SULPHONIC ACID

Cross Reference to Related Applications

This application is a national stage filing under section 371 of International Application No. PCT/FR2018/050653 filed on Mar. 19, 2018, and published on Sep. 27, 2018 as WO 2018/172677, which claims priority to French Application No. 1752289, filed on Mar. 20, 2017. The entire contents of WO 2018/172677 are hereby incorporated herein by reference.

FIELD OF THE INVENTION

The field of the invention relates to a new process for obtaining 2-acrylamido-2-methylpropane sulfonic acid. More precisely, the subject of the present invention is a production process for 2-acrylamido-2-methylpropane sulfonic acid consisting of co-reacting acrylonitrile, fuming sulfuric acid and isobutylene.

DESCRIPTION OF THE PRIOR ART

2-Acrylamido-2-methylpropane sulfonic acid is widely used as an additive in acrylic fibers and as a raw material for obtaining polymers used as dispersant, hydrogel or thickening agent in various sectors like the oil industry, construction, water treatment (desalination of seawater, mineral industry, etc.) or cosmetics.

The reaction used in the process for preparation of 2-acrylamido-2-methylpropane sulfonic acid follows the reaction scheme below in which acrylonitrile is present in excess so as to be both solvent for the reaction and a reagent. The acrylonitrile is brought into contact with fuming sulfuric acid (oleum) and isobutylene.

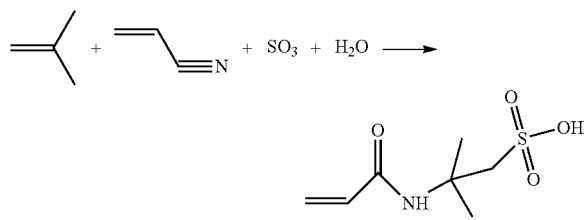

2-Acrylamido-2-methylpropane sulfonic acid is insoluble in the acrylonitrile solvent and consequently the reaction product takes the form of crystals suspended in the reaction solvent. However, 2-acrylamido-2-methylpropane sulfonic acid is soluble in water.

As examples, the documents U.S. Pat. No. 6,448,347 and CN 102,351,744 describe a new production process for 2-acrylamido-2-methylpropane sulfonic acid in continuous mode.

2-Acrylamido-2-methylpropane sulfonic acid is subsequently separated from the acrylonitrile, generally by filtration, and can later be purified by several known methods. In fact, purification is necessary because a low level of impurities present in 2-acrylamido-2-methylpropane sulfonic acid strongly affects polymerization thereof, and more specifically the molecular weight and the level of insolubles in the water from the resulting polymers and copolymers.

Thus, in the document WO 2009/072480, which covers a production process for 2-acrylamido-2-methylpropane sulfonic acid (ATBS), it is explained that 2-methyl-2-propenyl-1-sulfonic acid (IBSA) and 2-methylidene-1,3-propylene-disulfonic acid (IBDSA) type impurities above a certain concentration strongly affect polymerization.

The document U.S. Pat. No. 4,337,215 describes a 2-acrylamido-2-methylpropane sulfonic acid purification method by recrystallization in acetic acid, by hot dissolution and crystallization by progressive cooling. Despite the good purity of the resulting 2-acrylamido-2-methylpropane sulfonic acid, the process, whose yield is limited, calls for multiple steps of dissolution/cooling and requires the acetic acid used to be distilled to regenerate it before later reuse in a new 2-acrylamido-2-methylpropane sulfonic acid recrystallization batch.

Drying of 2-acrylamido-2-methylpropane sulfonic acid is necessary in order to reduce the remaining quantity of acrylonitrile and acrylamide present in the crystal. These two compounds are classified as carcinogenic, mutagenic or reprotoxic (CMR) and it is therefore necessary to do an effective filtration to best remove the acrylonitrile and then dry the product in order to obtain low acrylonitrile and acrylamide concentrations.

Document CN 103664709 discloses a 2-acrylamido-2-methylpropane sulfonic acid preparation process, overcoming the long and expensive drying step. An glacial acetic acid washing step, in which the ATBS is not soluble, substitutes this drying step. Although, this washing step allows to shorten the synthesis duration of 2-acrylamido-2-methylpropane sulfonic acid, solvent and thermal energy consumptions required to achieve such purification by recrystallization are still important.

As described in the article "On the Ritter synthesis of N-tert-butylacrylamide, reaction between tert-butyl alcohol and acrylonitrile in non-aqueous system" published in *Iranian J. of Polymer Science and Technology*, Vol. 4 No. 1, 1995, by Demetra Dragan, the 2-acrylamido-2-methylpropane sulfonic acid yield is linked to the free $SO_3$ ratio in the synthesis medium. Without being restricted to any theory, the more the medium is sulfonating, the more the reaction is selective to 2-acrylamido-2-methylpropane sulfonic acid to the detriment of N-tert-butylacrylamide.

There are many methods with which to obtain 2-acrylamido-2-methylpropane sulfonic acid. However, it seems accepted that it is important to improve the process for obtaining it by reducing the quality of solvent used and eliminating the drying step, or by decreasing the use of thermal energy, while keeping good 2-acrylamido-2-methylpropane sulfonic acid quality relating to the impurity levels thereof, to the capacity to be polymerized into high molecular weight polymer form or even to the level of carcinogenic, mutagenic or reprotoxic compounds.

SUMMARY OF THE INVENTION

The subject of the present invention is a production process for 2-acrylamido-2-methylpropane sulfonic acid including at least the following successive steps:
1) mixing of acrylonitrile with at least one compound contributing $SO_3$ at a temperature included between −80 and 30° C. for at least one second in order to obtain a sulfonating mixture;
2) placing in contact and mixing isobutylene and the sulfonating mixture with a molar ratio of $SO_3$ to isobutylene included between 0.2:1 and 2:1 and a molar ratio of acrylonitrile to isobutylene included between 3:1 and 60:1 at a temperature included between −40 and 100° C. for a time included between 10 seconds and 300 minutes in order to obtain a reaction mixture;
3) solid/liquid separation of the reaction mixture and isolation of the solid particles contained in the reaction mixture in the form of a composition 1 in which the solid particles represent 50 to 99% by weight of the composition 1;
4) mixing composition 1 with an aqueous solution A for at least 10 minutes at a temperature included between −20 and 70° C. in order to obtain a suspension 1 of 2-acrylamido-2-methylpropane sulfonic acid crystals;
5) solid/liquid separation of the suspension 1 and isolation of the crystals in the form of a composition 2 in which the crystals represent between 40 and 99% by weight of the composition 2.

The term "successive steps" refers to steps which follow a chronological order. In other words, the successive steps are realized in the indicated order and cannot be inverted. However, one or more intermediary steps may be inserted between two successive steps.

In the summary of the invention, the ranges of values include the boundary values. For instance, the range of values "between −40° C. and 80° C." includes −40° C. and 80° C. Moreover, the description discloses all possible combinations between the boundary values of the different ranges of values. As an example, the disclosure of ranges −80 to 30° C., preferably −40 to 10° C. includes ranges −80° C. to 10° C., 10° C. to 30° C., −80° C. to −40° C. or −40° C. to 30° C.

Step 1

The compound contributing $SO_3$ is generally fuming sulfuric acid, used at a concentration included between 100% and 113.5%. For example, fuming sulfuric acid at 113.5% includes 60% $SO_3$ by weight.

According to another embodiment, the compound contributing $SO_3$ and water can also be added separately. The alpha, beta or gamma forms of $SO_3$ can be used indistinguishably in the present invention. The water can also come from sulfuric acid having an $H_2SO_4$ concentration below 100%.

In another specific embodiment, $SO_3$ can be mixed with sulfuric acid.

In the scope of the present invention, acrylonitrile can be used in anhydrous form or in aqueous solution form thus contributing to the water balance of this step.

In the case where acrylonitrile is used in aqueous form, the reaction between the water contained in the acrylonitrile and the $SO_3$ compound produces sulfuric acid having an equivalent concentration of 96 to 103%.

$$\% \ H_2SO_4 \ \text{Effective} = \frac{m_{SO_3} * \% \ H_2SO_{4_{SO_3}} + m_{oleum} * \% \ H_2SO_{4_{oleum}} + m_{H_2SO_4} * \% \ H_2SO_4}{\frac{m_{ACN} * \% \ MC}{100} + m_{SO_3} + m_{oleum} + m_{H_2SO_4} + \sum_i \frac{m_j^{solvent \ i} + \% \ MC_i}{100}}$$

% $H_2SO_4$ effective: reflects the sulfuric acid concentration resulting from mixing acrylonitrile with at least one compound contributing $SO_3$
$m_{oleum}$: mass of oleum
% $H_2SO_4 \ _{oleum}$: concentration of oleum, expressed in % $H_2SO_4$.

$m_{SO_3}$: mass of $SO_3$
% $H_2SO_4 \ _{SO_3}$: concentration of $SO_3$, expressed in % $H_2SO_4$.
$m_{H2SO4}$: mass of sulfuric acid
% $H_2SO_4$: concentration of sulfuric acid, expressed in % $H_2SO_4$
$m_{ACN}$: mass of acrylonitrile
% MC: percentage by weight of water contained in the acrylonitrile
$m_i^{solvent \ i}$=mass of the solvent i
% $MC_i$=percentage of water by weight contained in the solvent i Usually the concentration of oleum is not expressed in % $H_2SO_4$ but in percentage of free $SO_3$. In which case the formula below is used for converting percentage $SO_3$ by weight into percentage $H_2SO_4$.

$$\% \ H_2SO_4 = 100 + \frac{(\% \ SO_3) * M_{H_2O}}{M_{SO_3}}$$

% $H_2SO_4$: concentration of sulfuric acid, expressed in % $H_2SO_4$
$M_{H_2O}$: molar mass of water
$M_{SO_3}$: molar mass of $SO_3$
% $SO_3$: percentage by weight of free $SO_3$ in the oleum.

In the specific case where $SO_3$ is used in gaseous form (pure or diluted in a carrier gas), the % $SO_3$ is 100%, therefore the corresponding % $H_2SO^4$ is 122.5%.

In a specific embodiment, step 1 includes mixing acrylonitrile with at least one compound contributing $SO_3$ in a solvent 1.

In a nonlimiting manner, the solvent 1 is chosen among acetic anhydride, carboxylic acids such as acetic acid nitriles, alcohols, amines, alkanes, amides, ethers, aromatics, alkylsulfonic acids and the liquid phase resulting from the liquid/solid separation from step 3). Preferably step 1) contains only acrylonitrile as solvent 1.

During this step, the mixing temperature is included between −80 and 30° C., preferentially comprised between −80 and 20° C., preferably included between −40 and 10° C.

The mixing time is advantageously included between 1 second and 600 minutes, preferably between 5 seconds and 120 minutes.

The mixing of reagents in step 1 can be done by various technologies. As examples and without limitation, we can cite reaction vessels with stirrers, loop reaction vessels, static mixers, microreactors and plug-flow reactors.

Step 2

During this step, isobutylene can be added to the sulfonating mixture in gaseous form, pure or diluted with a neutral gas (such as nitrogen or argon), or else in liquefied gas form, or dissolved in a solvent 2. Preferably isobutylene is added dissolved in a solvent 2. Preferably, this solvent 2 is acrylonitrile or the liquid phase resulting from the liquid/solid separation from step 3).

The reaction from addition of isobutylene can be done under atmospheric pressure or else under higher pressure, for example up to 50 bars relative.

Isobutylene can be made with various methods known to the person skilled in the art. As an example and without limitation, isobutylene can be obtained by dehydration of tert-butanol or isobutanol, by dehydrogenation of isobutane, by isomerization of but-1-ene or but-2-ene, by fermentation of glucose or waste from lignocellulose derivatives using microorganisms or by cracking methyl-tert-butyl ether (MTBE).

The molar ratio of $SO_3$ to isobutylene is included between 0.2:1 and 2:1 preferably between 0.4:1 and 1.5:1, and more preferably between 0.7:1 and 1.2:1.

The molar ratio between the $SO_3$ compound and isobutylene is defined as follows:

$$S{:}IB = \frac{\left[\dfrac{m_{SO_3}*\%\ H_2SO_{4_{SO_3}} + m_{oleum}*\%\ H_2SO_{4_{oleum}} + m_{H_2SO_4}^{\square}*\%\ H_2SO_{4_{\square\square}}^{\square}}{M_{H_2SO_4}}\right]/100}{\dfrac{m_{IB}}{M_{IB}}}$$

$$SO_3{:}IB = \frac{\left[\dfrac{m_{SO_3}*\%\ H_2SO_{4_{SO_3}} + m_{oleum}*\%\ H_2SO_{4_{oleum}} + m_{H_2SO_4}*\%\ H_2SO_4}{M_{H_2SO_4}}\right]/100}{\dfrac{m_{IB}}{M_{IB}}}$$

$m_{IB}$: mass of isobutylene
$M_{IB}$: molar mass of isobutylene
$SO_3$: quantity of moles of $SO_3$
IB: quantity of moles of isobutylene
$M_{H_2SO_4}$: molar mass of $H_2SO_4$ The other parameters $m_{oleum}$, % $H_2SO_{4_{oleum}}$, $m_{H_2SO_4}$, % $H_2SO_4$, $m_{SO_3}$, % $H_2SO_{4_{SO_3}}$ are the same as those previously described.

The molar ratio of acrylonitrile to isobutylene is included between 3:1 and 60:1 preferably between 4:1 and 40:1, and more preferably between 6:1 and 20:1.

The temperature is included between −40 and 100° C., preferably between −40 and 80° C., more preferably included between −20 and 70° C.

The time for mixing isobutylene and the sulfonating mixture from step 1) is included between 10 seconds and 300 minutes, preferably between 1 minute and 120 minutes.

The mixing of reagents in step 2) can be done by various technologies. As examples and without limitation, we can cite reaction vessels with stirrers, loop reaction vessels, static mixers, microreactors and plug-flow reactors.

During the addition of isobutylene in step 2), solid particles of 2-acrylamido-2-methylpropane sulfonic acid form and precipitate because they are no longer soluble in the sulfonating mixture coming from step 1). Consequently, the reaction product takes the form of a suspension of solid particles in the reaction mixture.

The reaction mixture, at the end of step 2), has a proportion of solids by weight advantageously included between 5 and 40%, more preferably between 10 and 35% and even more preferably between 15 and 30%.

The proportion of solids is defined as the following expression:

$$\text{Proportion of solids (\%)} = 100 * \frac{\dfrac{m_{IB}}{M_{IB}} * M_{ATBS}}{\sum_i m_i^{solvent\ i} + m_{SO_3} + m_{ACN} + m_{IB} + m_{Oleum} + m_{H_2O} + m_{H_2SO_4}}$$

$M_{ATBS}$: molar mass of 2-acrylamido-2-methylpropane sulfonic acid
$m_{H_2O}$: mass of water The other parameters ($m_i^{solvent\ i}$, $m_{SO_3}$, $m_{oleum}$, $m_{H_2SO_4}$, $m_{ACN}$, $m_{IB}$, $M_{IB}$) are the same as those previously described.

The reaction mixture can be immediately engaged in step 3 or else temporarily stored. The temporary storage of the reaction mixture can be done at a temperature advantageously below 50° C., more preferably below 25° C.

According to a specific embodiment, water can be added to the reaction mixture in order to consume the free $SO_3$ which was not consumed during the reaction. The water can be added in pure form or else in form of aqueous solution containing salts or soluble or miscible compounds. As an example and without limitation, the water can be added in the form of solution including acrylonitrile and/or 2-acrylamido-2-methylpropane sulfonic acid and/or an alcohol including from 1 to 4 carbon atoms and/or an inorganic acid.

Step 3

The 2-acrylamido-2-methylpropane sulfonic acid particles resulting at the end of step 2) are isolated using liquid/solid separation. As examples and without limitation, we can cite the use of a vertical or horizontal centrifuge, a decanter, a filter press, a belt filter, a disk filter, a pusher filter or rotary drum filter. The liquid/solid separation can also be done by gravity decanting.

In a specific embodiment, 2-acrylamido-2-methylpropane sulfonic acid particles can be concentrated in the reaction mixture by evaporation of solvents 1 and 2 before the solid/liquid separation step.

According to a specific embodiment of the invention, the liquid phase resulting from the separation can be used as solvent 1 and/or 2 in steps 1) and 2). This liquid phase can be used with or without prior purification. As examples of liquid phase purification techniques, we can cite fractional distillation, evaporation, pervaporation, neutralization with an organic or inorganic base and liquid/liquid extraction.

Preferably after the liquid/solid separation step, the 2-acrylamido-2-methylpropane sulfonic acid particles are not dried.

In practice, the 2-acrylamido-2-methylpropane sulfonic acid particles from the reaction mixture obtained at the end of step 2 are isolated in the form of composition 1 in which the 2-acrylamido-2-methylpropane sulfonic acid particles represent 50 to 99%, preferably between 50 and 97%, more preferably between 60 and 95%, more preferably between 70 and 90% by weight of the composition 1.

Generally, in the description, the rate of solid particles in the composition 1 represents the ratio between the total weight of 2-acrylamido-2-methylpropane sulfonic acid particles and the total weight of the composition 1. The remainder of the composition 1 can be composed of water, acrylonitrile, isobutylene, sulfuric acid or any other compound used during the process, or impurities formed during synthesis.

In this step, the 2-acrylamido-2-methylpropane sulfonic acid particle-based composition 1 can contain acrylonitrile.

According to a specific embodiment of the invention, the composition 1 can be washed with a solvent 3, preferably an acrylonitrile solution (with water or anhydrous). Advantageously, the quantity of washing solvent 3 used generally varies between 0.5 and 10 equivalents by weight relative to the quantity of solid 2-acrylamido-2-methylpropane sulfonic acid particles isolated.

Step 4

The reaction product in composition 1 in mixture with the aqueous solution A is in the form of a suspension, called suspension 1. In other words, in step 4), a part of the reaction product (solid particles) of the composition 1 is solubilized in the aqueous solution A and a part is not solubilized, which leads to the formation of the suspension 1. In practice, during the mixing of the composition 1 with the aqueous solution A, the aqueous phase is saturated in reaction product (solubilized solid particles). Therefore, the reaction product (solid particles) cannot entirely solubilize. Thus, a free-of-solid particles solution is never observed during step 4), since the aqueous phase is saturated, and solid particles of composition 1 remain in solid state, contrary to a recrystallization step.

Thanks to step 4), less solvent and less thermal energy are consumed compared to a recrystallization step such as the one described in U.S. Pat. No. 4,337,215 to which reference is made in CN 103664709. In fact, during a recrystallization, the crystals are solubilized and then recrystallized. The dissolution of crystals makes it possible to dissolve any impurities present in the crystals. Recrystallization makes it possible not to trap these impurities again in the crystals. Step 4) according to the invention is not comparable to recrystallization, since the solid particles are not all dissolved simultaneously, a suspension 1 being formed.

The mixing of the composition 1 with an aqueous solution A can be done with various technologies. As examples and without limitation, we can cite reaction vessels with stirrers, loop reaction vessels, static mixers, microreactors and plug-flow reactors.

There is no limitation on the order of addition of composition 1 and aqueous solution A. The composition 1 can be added first and then the aqueous solution A, or inversely.

In another embodiment, the composition 1 and the aqueous solution A can be added simultaneously.

The ratio by weight of aqueous solution A mixed with the composition 1 from step 3) is advantageously included between 0.05:1 and 1:1 (aqueous solution A/composition 1), and more preferably between 0.15:1 and 0.9:1.

Advantageously, the aqueous solution A can include up to 20% by weight of organic solvent 4, preferably from 0 to 15% by weight of organic solvent 4, more preferably from 2 to 10% by weight of organic solvent 4.

According to a specific embodiment of the invention, the aqueous solution A may include at least 80% by weight of water and up to 20% by weight of organic solvent 4, preferably between 85% and 100% by weight of water and from 0% 25 to 15% by weight of organic solvent 4, more preferably between 90% and 98% by weight of water and 2% to 10% by weight of organic solvent 4.

The organic solvent 4 is advantageously chosen from among carboxylic acids including 1 to 8 carbon atoms, amides including from 1 to 8 carbon atoms, alcohols 30 including from 1 to 8 carbon atoms, ketones including from 1 to 8 carbon atoms, ethers including from 1 to 8 carbon atoms, esters including from 1 to 8 carbon atoms, alkanes including from 1 to 8 carbon atoms, halogenated hydrocarbons containing from 1 to 8 carbon atoms, nitriles including from 1 to 8 carbon atoms or mixtures thereof. Preferably, solvent 4 is chosen among acrylonitrile, isopropanol, acetic acid and mixtures thereof. Preferably, the solvent 4 is acrylonitrile.

According to a specific embodiment of the invention, the aqueous solution A may include at least 80% by weight of water and up to 20% by weight of inorganic acid, preferably between 80% and 99% by weight of water and from 1% to 20% by weight of inorganic acid, more preferably between 85% and 98% by weight of water and 2% to 15% by weight of inorganic acid. Preferably the inorganic acid is sulfuric acid.

The aqueous solution A may also include an organic solvent 4, and an inorganic acid.

According to a specific embodiment, the aqueous solution A may include up to 55% by weight of 2-acrylamido-2-methylpropane sulfonic acid.

According to a specific embodiment of the invention, the mixing in step 4 may be done under an absolute pressure less than or equal to 1 bar. With this pressure, all or part of the solvent 4 and/or the inorganic acid and/or the water which could be present in the suspension 1 can be separated. This pressure can be used throughout the mixing or only partially.

The time for mixing aqueous solution A in composition 1 is advantageously included between 10 and 720 minutes, more preferably between 30 and 600 minutes.

The temperature while bringing into contact and mixing the aqueous solution A and the composition 1 is included between −20 and 70° C., preferably between −20° C. and 50° C., more preferably between 5° C. and 50° C. and even more preferably between 10° C. and 40° C. In another particular embodiment of the invention, the temperature may be comprised between 5° C. and 70° C.

The temperature is therefore lower than in the process described in document CN 103664709. It is, indeed, important that the reaction product in the composition 1 is not completely solubilized in the aqueous solution A, unlike the step of recrystallization of document CN 103664709.

Thus, during step 4), those skilled in the art will be able to adapt the temperature regarding the mass percentage of solid particles of the composition 1, and this, in order to obtain a suspension: the suspension 1.

After mixing, suspension 1 has an undissolved crystal content advantageously included between 10 and 85%, preferably between 20 and 40% by weight.

Step 5

The 2-acrylamido-2-methylpropane sulfonic acid crystals contained in suspension 1 and resulting at the end of step 4) are isolated by a liquid/solid separation step and have the form of a composition 2. As examples and without limitation, we can cite the use of a centrifugal filter, a decanter, a filter press, a belt filter, a disk filter, a closed filter under vacuum, a pressurized closed filter, or rotary drum filter. Preferably, the liquid solid separation is done using a centrifugal filter or Nutshe type closed filter.

The crystals resulting after this solid/liquid separation step can be used as is or else dried. As examples and without limitation, we can cite the use of all technologies for drying by convection, conduction or radiation (fluidized bed dryer, traversed bed, conveyor belt drying, microwave drying, drying by high-frequency radiation, infrared, spray drying).

The drying operation can be done at atmospheric pressure or under vacuum.

The drying operation can be done discontinuously (batch) or continuously.

Preferably the crystals are not dried after the liquid/solid separation step.

After isolation, composition 2 has a 2-acrylamido-2-methylpropane sulfonic acid crystal content included between 40 and 99%, preferably between 60 and 99%, more preferably between 60 and 98% by weight. The remainder of the composition includes principally water.

On the other hand, the liquid phase resulting following liquid/solid separation principally contains water and 2-acrylamido-2-methylpropane sulfonic acid at saturation and minority constituents of the organic solvent 1 and/or 2 and/or 3 and/or 4 or the inorganic acid. According to a specific embodiment of the invention, after separation this liquid phase can be fully or partially used in the aqueous solution A in step 4).

Step 6

In optional step 6), the composition 2 containing the crystals resulting at the end of step 5) is washed using a washing solution.

The washing solution is an aqueous solution which can include up to 20% by weight of organic solvent 4.

Preferably, the washing solution includes at least 80% by weight of water and up to 20% by weight of organic solvent 4, more preferably between 80% and 99% by weight of water and from 1% to 20% by weight of organic solvent 4, and even more preferably between 85% and 98% by weight of water and 2% to 15% by weight of organic solvent 4.

As already stated, organic solvent 4 is advantageously chosen from among acids including 1 to 8 carbon atoms, amides including from 1 to 8 carbon atoms, alcohols including from 1 to 8 carbon atoms, ketones including from 1 to 8 carbon atoms, ethers including from 1 to 8 carbon atoms, esters including from 1 to 8 carbon atoms, alkanes including from 1 to 8 carbon atoms, halogenated hydrocarbons containing from 1 to 8 carbon atoms, nitriles including from 1 to 8 carbon atoms or mixtures thereof. Preferably, the solvent is chosen among acrylonitrile, isopropanol, acetic acid or mixtures thereof; more preferably the solvent 4 is acrylonitrile.

According to a specific embodiment of the invention, the washing of composition 2 resulting at the end of step 5) can be done by spraying the washing solution on said composition 2.

According to another specific embodiment of the invention, the washing of the composition 2 resulting at the end of step 5) can be done by suspending the composition 2 in the washing solution.

The ratio by weight of the aqueous washing solution and composition 2 resulting at the end of step 5) is advantageously included between 0.05:1 and 10:1 (aqueous washing solution/composition 2) and preferably between 0.1:1 and 5:1.

The 2-acrylamido-2-methylpropane sulfonic acid crystals resulting at the end of this optional sixth step are advantageously isolated from the washing solution, for instance by a liquid/solid separation step, in the form of a composition 3. As examples and without limitation, we can cite the use of a vertical or horizontal centrifuge, a decanter, a filter press, a belt filter, a disk filter, a pusher filter, a closed filter under vacuum, a pressurized closed filter, a double-cone dryer or rotary drum filter. The liquid/solid separation can also be done by gravity decanting.

According to a specific embodiment of the invention, the recovered washing solution can wholly or partially be reused in step 6) with or without a prior treatment step.

According to a specific embodiment, the washing solution A may include up to 55% by weight of 2-acrylamido-2-methylpropane sulfonic acid.

According to a specific embodiment of the invention, the recovered washing solution can wholly or partially be used in the aqueous solution A in step 4) with or without a prior treatment step.

Step 7

In optional step 7), the composition 3 resulting at the end of step 6) is dried. As examples and without limitation, we can cite the use of all technologies for drying by convection, conduction or radiation (fluidized bed dryer, traversed bed, conveyor belt drying, microwave drying, drying by high-frequency radiation, infrared, spray drying).

The drying operation can be done at atmospheric pressure or under vacuum.

The drying operation can be done discontinuously (batch) or continuously.

During the production process, and whatever the step, it is possible to add at least one polymerization inhibitor. The inhibitor can be chosen without limitation among hydroquinone, p-methoxyphenol, phenothiazine, (2,2,6,6-tetramethylpiperidin-1-yl)oxyl, 4-hydroxy-2,2,6,6-tetramethylpiperidin-1-oxyl, phenylenediamine derivatives, or mixtures thereof.

Preferably the inhibitor is p-methoxyphenol.

The quantity of inhibitor added relative to the quantity of particles included in the composition 1 resulting at the end of step 3 is preferably included between 0.001% and 5% by weight, preferably between 0.01% and 1% by weight.

The inhibitor can be added during any one of the process steps, like for example by the use of p-methoxyphenol stabilized acrylonitrile. Preferably an additional quantity is added during step 4), more preferably the inhibitor is part of the aqueous solution A added in step 4).

The process can be done continuously or discontinuously (in batch).

The invention and the advantages resulting from it will be brought out more clearly by the following examples given to illustrate the invention and without limitation.

EXAMPLES OF THE INVENTION

Protocol for Preparation of
2-Acrylamido-2-Methylpropane Sulfonic Acid

Example 1

1522 g of acrylonitrile containing 0.4% by weight of water and 180 g of fuming sulfuric acid titrating 104% $H_2SO_4$ (18% oleum) were added to a stirred 2000 mL double-wall reaction vessel. The resulting sulfonating mixture was stirred for one hour and cooled by the double wall of the reaction vessel which kept the temperature of the sulfonating mixture at −20° C.

97 g of isobutylene was added to the preceding sulfonating mixture at a flow rate of 1.6 g per minute. The temperature of the resulting reaction mixture was held at 45° C. during addition of the isobutylene. The 2-acrylamido-2-methylpropane sulfonic acid particles precipitated in the reaction mixture and the proportion of solids was about 20% by weight.

The reaction mixture was filtered on a Büchner type filter; the resulting composition 1 contained 70% particles.

100 g of water, representing the aqueous solution A, was placed in a 500 mL stirred reaction vessel. The composition 1 recovered on the Büchner filter was added to the reaction vessel to obtain a suspension 1. The temperature was held at room temperature, meaning 25° C.

After four hours in suspension, the resulting suspension 1 was filtered on a Büchner type filter. The resulting composition 2 was not dried and 148 g of ATBS was recovered. The yield was 40% relative to the isobutylene.

322 g of liquid containing water, acrylonitrile, sulfuric acid and 2-acrylamido-2-methylpropane sulfonic acid was recovered.

Example 2

The conditions for obtaining composition 1 were identical to example 1.

100 g of liquid resulting at the end of example 1, representing the aqueous solution A, was placed in a 500 mL stirred reaction vessel. Composition 1, undried on the Büchner filter, was added to the reaction vessel. The temperature was held at room temperature, meaning 25° C.

After three hours in suspension, the resulting suspension 1 was filtered on a Büchner type filter. The resulting composition 2 was undried and 340 g of ATBS was recovered. The yield was 91% relative to the isobutylene.

138 g of liquid containing water, acrylonitrile, sulfuric acid and 2-acrylamido-2-methylpropane sulfonic acid was recovered.

Example 3

1215 g of acrylonitrile containing 0.2% by weight of water, 130 g of sulfuric acid (98% concentration) and 130 g of fuming sulfuric acid titrating 105.62% $H_2SO_4$ (25% oleum) were added to a stirred 2000 mL double-wall reaction vessel. The resulting sulfonating mixture was stirred for one hour and cooled by the double wall of the reaction vessel which kept the sulfonating mixture at −20° C.

135 g of isobutylene was added to the preceding sulfonating mixture at a flow rate of 1 g per minute. The temperature of the resulting reaction mixture was held at 40° C. during addition of the isobutylene. The 2-acrylamido-2-methylpropane sulfonic acid particles precipitated in the reaction mixture and the proportion of solids was about 30% by weight.

The reaction mixture was filtered on a Büchner type filter; the resulting composition 1 contained was 70% crystals.

120 g of water, representing the aqueous solution A, was placed in a stirred 1000 mL reaction vessel. The composition 1 recovered on the Büchner filter was added to the reaction vessel to obtain a suspension 1. The temperature was held at room temperature, meaning 25° C.

After three hours in suspension, the resulting suspension 1 was filtered on a Büchner type filter. The resulting composition 2 was not dried and 250 g of ATBS was recovered. The yield was 50% relative to the isobutylene.

386 g of liquid containing water, acrylonitrile, sulfuric acid and 2-acrylamido-2-methylpropane sulfonic acid was recovered.

Example 4

1215 g of acrylonitrile containing 0.3% by weight of water, 100 g of sulfuric acid (96% concentration) and 130 g of fuming sulfuric acid titrating 105.18% $H_2SO_4$ (23% oleum) were added to a stirred 2000 mL double-wall reaction vessel. The resulting sulfonating mixture was stirred for 10 min. and cooled by the double wall of the reaction vessel which kept the sulfonating mixture at −20° C.

125 g of isobutylene was added to the preceding sulfonating mixture at a flow rate of 1 g per minute. The temperature of the resulting reaction mixture was held at 40° C. during addition of the isobutylene. The 2-acrylamido-2-methylpropane sulfonic acid particles precipitated in the reaction mixture and the proportion of solids was about 30% by weight.

The reaction mixture was filtered on a Büchner type filter; the resulting composition 1 contained was 70% crystals.

110 g of water, representing the aqueous solution A, was placed in a 500 mL stirred reaction vessel. The composition 1 recovered on the Büchner filter was added to the reaction vessel to obtain a suspension 1. The temperature was held at room temperature, meaning 25° C.

After three hours in suspension, the resulting suspension 1 was filtered on a Büchner type filter. The resulting composition 2 was not dried and 235 g of ATBS was recovered. The yield was 49% relative to the isobutylene.

354 g of liquid containing water, acrylonitrile, sulfuric acid and 2-acrylamido-2-methylpropane sulfonic acid was recovered.

The invention claimed is:

1. A production process for 2-acrylamido-2-methylpropane sulfonic acid including at least the following successive steps:
   1) mixing of acrylonitrile with at least one compound contributing $SO_3$ at a temperature included between −80 and 30° C. for at least one second in order to obtain a sulfonating mixture;
   2) placing in contact and mixing isobutylene and the sulfonating mixture with a molar ratio of $SO_3$ to isobutylene included between 0.2:1 and 2:1 and a molar ratio of acrylonitrile to isobutylene included between 3:1 and 60:1 at a temperature included between −40 and 100° C. for a time included between 10 seconds and 300 minutes in order to obtain a reaction mixture;
   3) solid/liquid separation of the reaction mixture and isolation of the solid particles contained in the reaction mixture in the form of a composition 1 in which the solid particles represent 50 to 99% by weight of the composition 1;
   4) mixing composition 1 at the end of step 3) with an aqueous solution A for at least 10 minutes at a temperature included between −20 and 70° C. in order to obtain a suspension 1 of 2-acrylamido-2-methylpropane sulfonic acid crystals;
   5) solid/liquid separation of the suspension 1 and isolation of the crystals in the form of a composition 2 in which the crystals represent between 40 and 99% by weight of the composition 2.

2. The process according to claim 1, wherein the compound contributing $SO_3$ is fuming sulfuric acid, used at a concentration included between 100% and 113.5%.

3. The process according to claim 1, wherein step 1) includes mixing acrylonitrile with at least one compound contributing $SO_3$ in a solvent 1.

4. The process according to claim 3, wherein the solvent 1 is acrylonitrile.

5. The process according to claim 1, wherein isobutylene is added, during step 2), dissolved in a solvent 2.

6. The process according to claim 1, wherein the molar ratio of $SO_3$ to isobutylene from step 2) is included between 0.4:1 and 1.5:1.

7. The process according to claim 5, wherein 2-acrylamido-2-methylpropane sulfonic acid particles are concentrated in the reaction mixture by evaporation of solvents 1 and 2 before the solid/liquid separation step.

8. The process according to claim 1, wherein the ratio by weight of aqueous solution A mixed, during step 4), with the composition 1 from step 3) is included between 0.05:1 and 1:1.

9. The process according to claim 1, wherein composition 1 is washed with a solvent 3.

10. The process according to claim 1, wherein the aqueous solution A of step 4) includes up to 20% of organic solvent 4.

11. The process according to claim 10, wherein the organic solvent 4 is acrylonitrile.

12. The process according to claim 1, wherein the aqueous solution A from step 4) includes at least 80% by weight of water and up to 20% by weight of inorganic acid.

13. The process according to claim 12, wherein the inorganic acid is sulfuric acid.

14. The process according to claim 1, wherein the liquid phase resulting at the end of the solid/liquid separation of the suspension 1 in step 5) serves wholly or partially as aqueous solution A in step 4).

15. The process according to claim 1, wherein the composition 2 of step 5) is washed using a washing solution.

16. The process according to claim 3, wherein the solvent 1 is chosen from the group including acetic anhydride, carboxylic acids, acetic acid, nitriles, alcohols, amines, alkanes, amides, ethers, aromatics, alkylsulfonic acids and the liquid phase resulting from the liquid/solid separation from step 3).

17. The process according to claim 5, wherein the solvent 2 is selected from acrylonitrile and the liquid phase resulting from the liquid/solid separation from step 3).

18. The process according to claim 6, wherein the molar ratio of $SO_3$ to isobutylene from step 2) is included between 0.7:1 and 1.2:1.

19. The process according to claim 8, wherein the ratio by weight of aqueous solution A mixed, during step 4), with the composition 1 from step 3) is included between 0.15:1 and 0.9:1.

20. The process according to claim 1 wherein:
composition 1 is washed with a solvent 3, which is an acrylonitrile solution;
the aqueous solution A of step 4) includes: from 2 to 10% of organic solvent 4, wherein the organic solvent 4 is acrylonitrile; between 85% and 98% by weight of water; and 2% to 15% by weight of inorganic acid, wherein the organic acid is sulfuric acid; and
the composition 2 of step 5) is washed using a washing solution, which is an aqueous solution including up to 20% by weight of organic solvent 4.

* * * * *